United States Patent
Liu et al.

(10) Patent No.: US 9,687,516 B2
(45) Date of Patent: Jun. 27, 2017

(54) PREPARATION METHOD FOR EXTRACTIVE OF JINXUAN HEMORRHOID WASHING POWDER BOTANICALS

(75) Inventors: Yanwen Liu, Wuhan (CN); Shuhe Chen, Wuhan (CN); Hui Wang, Wuhan (CN); Yaping Li, Wuhan (CN); Lu Zhou, Wuhan (CN); Wenying Zhang, Wuhan (CN); Wei Liu, Wuhan (CN)

(73) Assignee: Mayinglong Pharmaceutical Group Co., Ltd., Wuhan, Hubei (CN)

( * ) Notice: Subject to any disclaimer, the term of this patent is extended or adjusted under 35 U.S.C. 154(b) by 320 days.

(21) Appl. No.: 14/110,611

(22) PCT Filed: Mar. 8, 2012

(86) PCT No.: PCT/CN2012/072093
§ 371 (c)(1),
(2), (4) Date: Oct. 9, 2013

(87) PCT Pub. No.: WO2012/119560
PCT Pub. Date: Sep. 13, 2012

(65) Prior Publication Data
US 2014/0087010 A1    Mar. 27, 2014

(30) Foreign Application Priority Data
Mar. 8, 2011 (CN) .......................... 2011 1 0055689

(51) Int. Cl.
| | | |
|---|---|---|
| *A61K 36/36* | (2006.01) | |
| *A61K 36/538* | (2006.01) | |
| *A61K 36/355* | (2006.01) | |
| *A61K 9/00* | (2006.01) | |

(52) U.S. Cl.
CPC .......... *A61K 36/538* (2013.01); *A61K 9/0031* (2013.01); *A61K 36/355* (2013.01); *A61K 36/36* (2013.01); *A61K 2236/00* (2013.01)

(58) Field of Classification Search
None
See application file for complete search history.

(56) References Cited

FOREIGN PATENT DOCUMENTS

| CN | 102133265 A | 7/2011 |
|---|---|---|
| CN | 102133266 A | 7/2011 |

OTHER PUBLICATIONS

Zhou, Lu et al., "Components of Active Sites of Jinxuan Zhike Xunxi San and Anti-Inflammatory and Analgesic Effect of Original Preparation", Herald of Medicine, Apr. 2010, pp. 439-441, vol. 29, No. 4.
Wang, Hui et al., "Determination of the Content of Flavonoids and Saponins in Anti-Inflammatory and Active Sites in Jinxuan San", Guide of China Medicine, Jul. 2010, pp. 53-55, vol. 8, No. 21.
Zhang, Wenying et al., "Study on Active Sites of Anti-Inflammatory and Analgesic in Jinzuan Zhike Xunxi San", Chinese Journal of Information on Tranditional Chinese Medicine, Feb. 2010, pp. 35-37, vol. 17, No. 2.

*Primary Examiner* — Terry A McKelvey
*Assistant Examiner* — Catheryne Chen
(74) *Attorney, Agent, or Firm* — Muncy, Geissler, Olds & Lowe, P.C.

(57) ABSTRACT

A preparation method for extractive botanicals includes: (A) honeysuckle, schizonepeta, and purslane in a powder are mixed, ground, and passed through a mesh; the medicinal powder obtained from supercritical extraction is soaked in alcohol, then undergoes percolation extraction, and the percolate is collected; (B) the alcohol percolate is concentrated, left stand, and suction filtrated to obtain a filtrate; (C) the filtrate macroporously adsorbs to a resin column at a flow velocity, is then removed of impurity by water washing, and undergoes elution with alcohol to obtain an alcohol eluent; (D) alcohol is recovered from the eluent, the remaining liquid is concentrated, and the concentrated liquid is dried to obtain the extractive of botanicals. The total content of flavones, saponins, and organic acids exceeds 70%. The extractive has substantial anti-inflammatory and pain relieving effects.

8 Claims, 3 Drawing Sheets

PREPARATION METHOD FOR EXTRACTIVE OF JINXUAN HEMORRHOID WASHING POWDER BOTANICALS

FIELD OF THE INVENTION

The present invention relates to technical field of extracting and purifying active parts of Chinese medicine compounds, more specifically relates to a preparation method for extractive of Jinxuan Hemorrhoid Washing Powder botanicals.

BACKGROUND OF THE INVENTION

Jinxuan Hemorrhoid Washing Powder is a Chinese medicine variety produced by Wuhan Mayinglong Pharmaceutical Company. The Chinese medicine is prepared by five flavors of Chinese medicine compositions—Xuan Ming powder, dried alum, honeysuckle, schizonepeta, and purslane, with effects of swelling and pain relieving, and dispelling pathogenic wind and removing dampness; clinically used for the treatment of anus inflammation, swelling, pain and other symptoms caused by inflammatory external hemorrhoids and hemorrhoid operations, having rapid onset, good curative effect, easy to use and other features. Therefore, this variety of Chinese medicine is quite popular in the majority of patients, and has a broad market prospect. However, this variety of Chinese medicine compound is prepared by a traditional production process, and is accompanied with many inadequacies, which includes unclear active material basis, imperfect quality control standard, not yet stable drug efficacy, relatively large dosages for clinical use, and the topical health conditions need to be improved.

The Jinxuan Hemorrhoid Washing Powder compound is comprised of three flavors of botanicals—honeysuckle, schizonepeta and purslane and two flavors of minerals. There are relatively more researches on chemical components: honeysuckle mainly contains flavones, triterpene glycosides, organic acids, volatile oils and other components; schizonepeta mainly contains volatile oils, flavones, phenolic acids and other components; purslane mainly contains organic acids, flavones, volatile oils and other components; Xuan Ming powder mainly contains sodium sulfate ($Na_2SO_4$), and dried alum is made by alumen calcining, with $KAl(SO_4)_2$ as its main component.

Modern pharmacological studies have shown that honeysuckle has anti-inflammatory, anti-endotoxin, anti-bacteria and anti-virus, anti-tumor and other effects, with total flavones, total saponins and organic acids as its main active ingredients; schizonepeta has anti-inflammatory and analgesic, anti-virus, anti-bacteria, and other effects, with flavones and polyphenols substances as its main active ingredients; purslane has anti-bacteria and anti-virus, anti-tumor, immune function adjusting, anti-aging and other effects, with flavones and organic acids as its main active ingredients.

The aforementioned active ingredients in the botanicals in the original Jinxuan Hemorrhoid Washing Powder prescription are usually extracted by water-adding decoction method which has drawbacks of extracts containing many impurities, big loss of active ingredients, efficacy substances' instability, high cost, environmental pollution etc., and thus does not meet the requirements of Chinese medicine industrialization.

SUMMARY OF THE INVENTION

To solve the abovementioned technical problems, the present invention treats the three flavors of botanicals in the Jinxuan Hemorrhoid Washing Powder prescription as a whole, its medicinal powder after supercritical $CO_2$ extraction is percolation extracted using alcohol as extraction solvent, the extracted solution is purified through a macroporous resin to obtain relatively high contents of flavones, saponins and organic acids active substance parts, and there is no relevant information about such extraction and purification technology reported at home and abroad. Its extraction and purification process is simple, saves energy, controls the environmental pollution, reduces the security risks during production, and thus complies with the requirements of Chinese medicine industry modernization.

To achieve the aforementioned objects, the present invention employs the following technical measures:

A preparation method for extractive of Jinxuan Hemorrhoid Washing Powder botanicals, comprising the following steps:

(a) The three flavors of botanicals—honeysuckle, schizonepeta, and purslane in the prescription of Jinxuan Hemorrhoid Washing Powder are mixed at a weight ratio of 3:4:3, ground, and passed through a 30-50 mesh, the medicinal powder obtained from supercritical extraction is added with an alcohol aqueous solution with a weight of 2-4 times that of said medicinal powder and a volume ratio of 30~90% and Soaked for 20-30 hours, and then an alcohol aqueous solution with a volume ratio of 30~90% is added to make the weight of the alcohol aqueous solution with a volume ratio of 30~90% equal to 6~14 times the weight of said medicinal powder, percolation extraction is underwent with a flow velocity the weight of 1~5 times that of said medicinal powder per hour, and the percolate is collected;

(b) The alcohol percolate obtained in step (a) is concentrated to a weight of 1~5 times that of said medicinal powder, left stand for 2~10 h, and suction filtrated to obtain a filtrate;

(c) The filtrate macroporously absorbs to a resin column at a flow velocity of a volume of 0.5~4 times that of the column per hour, is then removed of impurity by washing with water with a volume of 2~4 times that of the column, and undergoes elution with an alcohol aqueous solution with a volume ratio of 40~95% and a flow velocity of a volume of 0.5~4 times that of the column per hour to obtain an alcohol eluent; and (d) Alcohol is recovered from the eluent, the remaining liquid is concentrated, and the concentrated liquid is dried to obtain the extractive of Jinxuan Hemorrhoid Washing Powder botanicals.

Preferably, in step (a), the medicinal powder obtained from supercritical extraction is added with an alcohol aqueous solution with a weight of 3 times that of said medicinal powder and a volume ratio of 50% and soaked for 24 hours, and then a 50% alcohol aqueous solution is added to make the weight of the 50% alcohol aqueous solution equal to 12 times the weight of the medicinal powder, percolation extraction is underwent with a flow velocity of the weight of 2 times that of the medicinal powder per hour, and the percolate is collected.

Preferably, in step (b), the percolate obtained is concentrated to a weight of 3.3 times that of said medicinal powder.

Preferably, in step (c), the filtrate macroporously absorbs to a resin column at a flow velocity of a volume of 1 time that of the column per hour, is then removed of impurity by washing with water with a volume of 3 times that of the column, and subsequently the active substances in said macroporous resin column are eluted with an alcohol aqueous solution with a volume of 5 times that of the column, a volume ratio of 70%, a flow velocity of a volume of 1 time that of the column per hour.

Preferably, in step (d), the dry method is spray drying, and the conditions are: inlet temperature of 170° C., outlet temperature of 90° C., and atomizing disk rotation speed of 20,000 µM.

Preferably, said macroporous resin column is a medicinal model D101 type macroporous resin column.

Preferably, the diameter-height ratio of said macroporous resin column is 1:3~1:8.

Preferably, the supercritical extraction step in step (a): the grounded three flavors of botanicals are put into the supercritical $CO_2$ extraction device with extraction temperature of 45° C., extraction pressure of 25 MPa and extraction time of 90 min, to obtain the medicinal powder after supercritical extraction.

The present invention also provides medically acceptable formulations prepared from the extractive of Jinxuan Hemorrhoid Washing Powder botanicals obtained by the aforementioned method, comprising: smoked lotions, tablets, capsules, buccal tablets, granules, electuaries, pills, powders, ointments, sublimed preparations, suspensions, powders, solutions, injections, suppositories, creams, sprays, drops, and patches.

Preferably, a medically acceptable carrier is added when said extractive of Jinxuan Hemorrhoid Washing Powder botanicals is formulated to a pharmaceutically acceptable formulation, said medically acceptable carrier is one of the group consisting of starch, sucrose, lactose, mannitol, cellulose and its derivatives, alginates, gelatin, polyvinylpyrrolidone, glycerol, polysorbate 80, agar, calcium carbonate, calcium bicarbonate, a surfactant, polyethylene glycol, cyclodextrin, kaolin, talc, calcium stearate or magnesium stearate.

The present invention, when compared with prior art, has the following advantages and effects:

The present invention uses alcohol as extraction solvent, the extracted solution is purified through a macroporous resin, and there is no relevant information about the preparation process of the extraction of active substances sites is reported at home and abroad. Its extraction and purification process is simple, produces high active substance content at a lower production cost and energy consumption, controls the environmental pollution, reduces the security risks during production, and thus complies with the requirements of Chinese medicine industry modernization. The total content of flavones, saponins, and organic acids can exceed 70% of the weight of the extractive. The macroporous resin used can be repeatedly used, and results shows that the extractive of Jinxuan Hemorrhoid Washing Powder botanicals has substantial anti-inflammatory and pain relieving effects.

The present invention employs a research method combining orthogonal design tests with single factor. Systematic studies on the alcohol percolation extraction process and the D101 macroporous resin purification process of the flavone, saponin and organic acid ingredients on the non-volatile active substance parts of Jinxuan Hemorrhoid Washing Powder prescription has been done, to obtain a reliable technical parameters, test on a pilot plant scale and make the transition to industrialization possible. Thus, the present invention has relatively strong application value.

The extractive prepared by Example 3 of the present invention has evident pharmacological test effects, and its anti-inflammatory and analgesic effect can be seen in Table 1-Table 3.

TABLE 1

Effects of Extractive of Jinxuan Hemorrhoid Washing Powder Botanicals on Rat's Foot Swelling Induced by Egg White

| Group | Animal number | Dosage (g raw drug/ml) | Original foot volume (ml) | Foot swelling degree (%) | | | |
|---|---|---|---|---|---|---|---|
| | | | | 1 hour | 2 hours | 4 hours | 7 hours |
| Negative group | 10 | — | 1.08 ± 0.14 | 75.8 ± 15.2 | 86.5 ± 30.0 | 61.1 ± 10.4 | 60.9 ± 26.9 |
| High-dosage extractive group | 10 | 0.52 | 1.03 ± 0.12 | 80.8 ± 17.2 | 67.5 ± 21.2 | 60.9 ± 20.4 | 42.3 ± 15.9 |
| Low-dosage extractive group | 10 | 0.26 | 0.99 ± 0.07 | 73.8 ± 18.2 | 69.3 ± 21.5 | 69.9 ± 21.2 | 36.6 ± 18.3★ |

Note:
Compared with the negative group, P < 0.05; P < 0.01▲

TABLE 2

Effects of Extractive of Jinxuan Hemorrhoid Washing Powder Botanicals on Mouse's Ear Swelling Induced by Xylene

| Group | Animal number | Dosage (g raw drug/ml) | Left ear weight (mg) | Ear swelling degree (%) |
|---|---|---|---|---|
| Negative group | 10 | — | 6.29 ± 0.31 | 127.2 ± 39.68 |
| High-dosage extractive group | 10 | 1.04 | 6.33 ± 0.74 | 91.19 ± 40.78★ |
| Low-dosage extractive group | 10 | 0.52 | 6.11 ± 0.69 | 130.9 ± 43.57 |

Note:
Compared with the negative group, P < 0.05; P < 0.011▲

TABLE 3

Effects of Extractive of Jinxuan Hemorrhoid Washing Powder Botanicals on Mouse's Pain Threshold Induced by Hot Plate

| Group | Animal number | Dosage (g raw drug/ml) | Basic pain threshold (s) | Pain threshold at each time point (s) | | |
|---|---|---|---|---|---|---|
| | | | | 30 min | 60 min | 90 min |
| Negative group | 12 | — | 22.7 ± 5.24 | 23.6 ± 12.2 | 33.5 ± 10.5 | 25.8 ± 15.7 |
| High-dosage extractive group | 12 | 1.04 | 23.0 ± 6.16 | 46.9 ± 12.2▲ | 41.8 ± 15.9 | 36.6 ± 17.8 |
| Low-dosage extractive group | 12 | 0.52 | 22.6 ± 4.68 | 52.3 ± 11.6▲ | 21.2 ± 7.8 | 35.3 ± 9.1 |

Note:
Compared with the negative group, $P < 0.05$; $P < 0.01$▲

DESCRIPTION OF THE ACCOMPANYING DRAWINGS

SPECIFIC EMBODIMENTS

Figure 1:
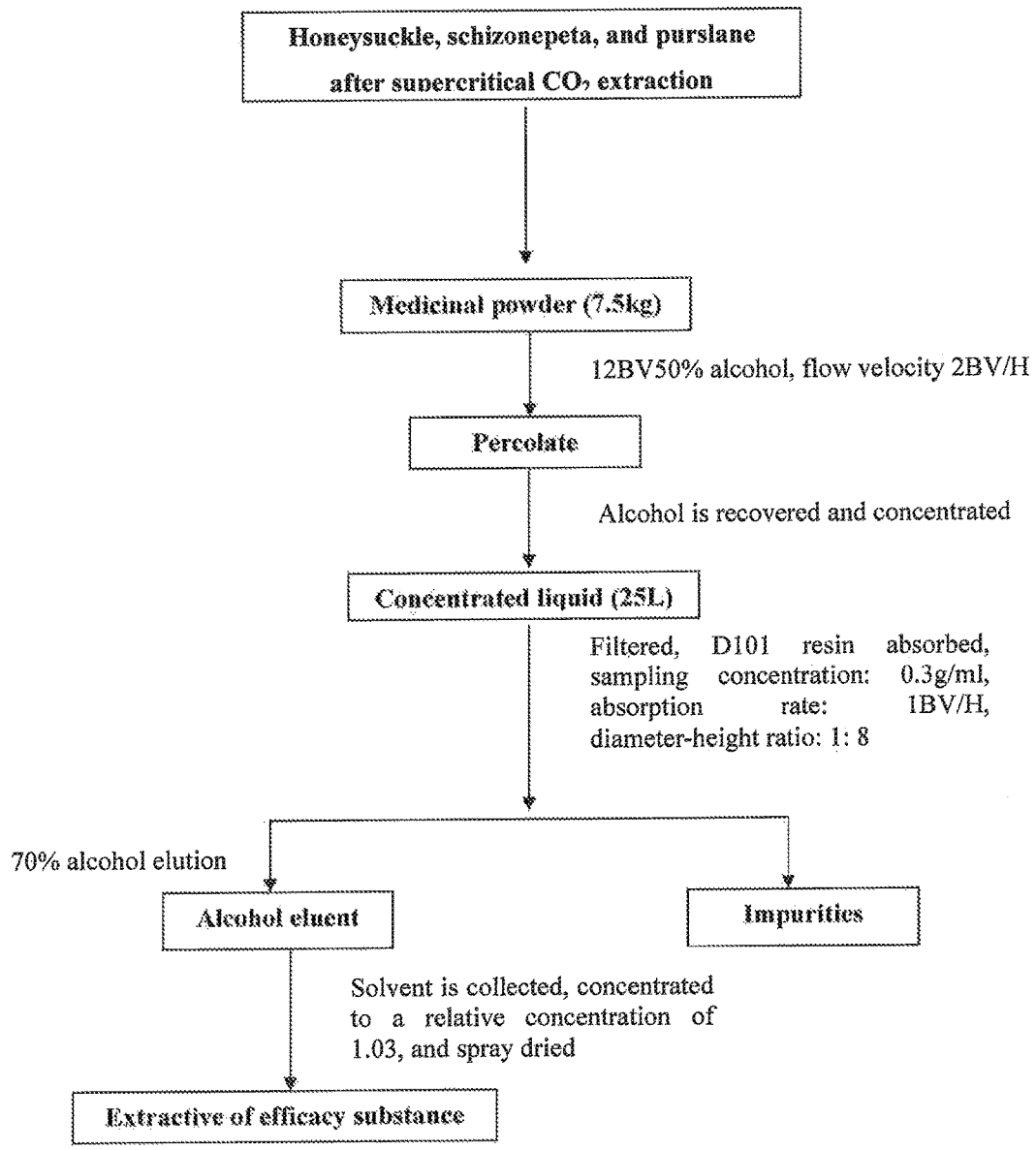
FIG. 1 is the extracting and purifying process flow diagram of the extractive of Jinxuan Hemorrhoid Washing Powder botanicals.

In combination with what is shown in FIG. 1, the present invention provides a preparation method for extractive of Jinxuan Hemorrhoid Washing Powder botanicals, comprising the following steps:

(a) The three flavors of botanicals—honeysuckle, schizonepeta, and purslane in the prescription of Jinxuan Hemorrhoid Washing Powder are mixed at a weight ratio of 3:4:3, ground, and passed through a 40 mesh, the medicinal powder obtained from supercritical extraction (extraction conditions: put in supercritical $CO_2$ extraction device, extraction temperature 45° C., extraction pressure 25 MPa, extraction time 90 min. Extraction purposes: to remove soluble ingredients) is added with an 30~90% (volume ratio) alcohol aqueous solution with a weight of 2~4 times that of the medicinal powder (three flavors of botanicals) and soaked for 20~30 hours, and then an 30~90% (volume ratio) alcohol aqueous solution is added to make the weight of the 30~90% (volume ratio) alcohol aqueous solution equal to 6~14 times the weight of the medicinal powder (three flavors of botanicals), the percolation extraction is underwent with a flow velocity of the weight of 1~5 times that of the medicinal powder (three flavors of botanicals) per hour, and the percolate is collected;

(b) The alcohol percolate obtained in step (a) is concentrated to a weight of 1~5 times that of the medicinal powder (three flavors of botanicals), left stand (2~10 h), and suction filtrated to obtain a filtrate;

(c) The filtrate macroporously adsorpts to a resin column at a flow velocity of a volume of 0.5~4 times that of the column per hour, is then removed of impurity by washing with water with a volume of 2~4 times that of the column, and undergoes elution with an 40~95% (volume ratio) alcohol aqueous solution and a flow velocity of a volume of 0.5~4 times that of the column per hour to obtain an alcohol eluent; and (d) Alcohol is recovered from the alcohol eluent which is concentrated to a relative density (water=1) of 1.01~1.10, and the concentrated liquid is spray dried to obtain the extractive product of Jinxuan Hemorrhoid Washing Powder botanicals (extractive of the efficacy parts). The dried extraction is collected, sealed, weighed, and preserved in dry place. After determination, the total content of flavones, saponins, and organic acids in extractive of Jinxuan Hemorrhoid Washing Powder botanicals can exceed 70% of the weight of the extractive of Jinxuan Hemorrhoid Washing Powder botanicals.

As shown in FIG. 1, the preparation method procedure of the extractive of Jinxuan Hemorrhoid Washing Powder botanicals in a more preferable example of the present invention is: 7.5 Kg medicinal powder obtained from supercritical extraction of the three flavors of Jinxuan Hemorrhoid Washing Powder botanicals (which is mixed at a ratio of 3:4:3, ground, and passed through a 40 mesh) is added with a 50% (volume ratio) alcohol aqueous solution with a weight of 3 times that of the medicinal powder (three flavors of botanicals) and soaked for 24 hours, and then a 50% (volume ratio) alcohol aqueous solution is added to make the weight of the 50% (volume ratio) alcohol aqueous solution equal to 12 times the weight of the medicinal powder (three flavors of botanicals), the percolation extraction is underwent with a flow velocity of the weight of 2 times that of the medicinal powder (three flavors of botanicals) per hour, and the percolate is collected; the percolate is concentrated to a certain volume to make the weight of the drug solution equal to 3.3 times that of said medicinal powder (25 L), left stand, and suction filtrated to obtain a sampling drug solution for future use. The sampling drug solution is absorbed at a flow velocity of 1 Bv/h (diameter-height ratio of the resin bed is 1:8), following absorption, it is washed with distilled water with a volume of 3 times that of the resin column at a flow velocity of 1 Bv/h and underwent elution with an 70% alcohol aqueous solution with a volume of 5 times that of the resin column at a flow velocity of 1 Bv/h to obtain the eluent. Alcohol is recovered from the eluent which is concentrated to a relative density of 1.03, and spray dried, the dried extraction is collected, sealed, weighed, and preserved in shade place.

That is to say, the preferred extracting and purifying conditions of the preparation method of the extractive of Jinxuan Hemorrhoid Washing Powder botanicals in a more preferable example of the present invention are:

In step (a), 7.5 Kg medicinal powder obtained from supercritical extraction of the three flavors of Jinxuan Hemorrhoid Washing Powder botanicals (which is mixed at a ratio of 3:4:3, ground, and passed through a 40 mesh) is added with a 50% (volume ratio) alcohol aqueous solution with a weight of 3 times that of the medicinal powder (three flavors of botanicals) and soaked for 24 hours, and then a 50% (volume ratio) alcohol aqueous solution is added to make the weight of the 50% (volume ratio) alcohol aqueous solution equal to 12 times the weight of the medicinal powder (three flavors of botanicals), the percolation extraction is underwent with a flow velocity of the weight of 2 times that of the medicinal powder (three flavors of botanicals) per hour, and the percolate is collected.

In step (b), the concentrated drug solution of the alcohol percolate (100 L) has a weight of 3.3 times (25 L) that of the medicinal powder.

In step (c), the filtrate macroporously adsorpts to a resin column at a flow velocity of a volume of 1 time that of the column per hour, is then removed of impurity by washing with water with a volume of 3 times that of the column, and continues to undergo elution with an 70% (volume ratio) alcohol aqueous solution and a flow velocity of a volume of 1 time that of the column per hour to elute the efficacy substances in the resin.

In step (d), the conditions of spray drying are: inlet temperature of 170° C., outlet temperature of 90° C., and atomizing disk rotation speed of 20,000 R/M.

The total content of flavones, saponins, and tannins in extractive of Jinxuan Hemorrhoid Washing Powder botanicals can be up to 71.1% of the weight of the extractive of Jinxuan Hemorrhoid Washing Powder botanicals.

The concentration of the alcohol described in the present invention means the volume fragment of alcohol in 100 mL volume alcohol aqueous solution.

The present invention also provides a pharmaceutical composition, i.e. total flavones, total saponins, and total organic acids, prepared with the extractive of Jinxuan Hemorrhoid Washing Powder botanicals, and the application of the extractive of the present invention in anti-inflammatory and pain relieving drugs.

The aforementioned pharmaceutical composition of the present invention can be any medically accepted formulations which is comprised of: smoked lotions, tablets, sugar-coated tablets, film-coated tablets, enteric coated tablets, capsules, hard capsules, soft capsules, oral liquids, buccal tablets, granules, electuaries, pills, powders, ointments, sublimed preparations, suspensions, powders, solutions, injections, suppositories, soft ointments, hard ointments, creams, sprays, drops, and patches.

A medically acceptable carrier can be added to the aforementioned pharmaceutical composition when it is prepared to a dosage form. Said pharmaceutically acceptable carrier can be: starch, sucrose, lactose, mannitol, silicon derivatives, cellulose and its derivatives, alginates, gelatin, polyvinylpyrrolidone, glycerol, polysorbate 80, agar, calcium carbonate, calcium bicarbonate, surfactant, polyethylene glycol, cyclodextrin, phospholipid material, kaolin, talc powder, calcium stearate, magnesium stearate, etc.

The present invention will be further described below with reference to the examples.

Example 1

Percolation Extraction Process Test of Active Ingredients of the Three Flavors of Botanicals—Honeysuckle, Schizonepeta, and Purslane in Jinxuan Hemorrhoid Washing Powder Prescription Using Alcohol as Solvent (1) Alcohol percolation extraction process test: percolation extraction process studies have been done to the effective substances contained in the medicinal powder (50 g) obtained from supercritical $CO_2$ extraction of the three flavors of Jinxuan Hemorrhoid Washing Powder botanicals (which is mixed at a ratio of 3:4:3, ground, and passed through a 40 mesh) in the present test. Four factors and three levels orthogonal table experimental method is employed, the alcohol concentration in the solvent, the dose of alcohol, the percolation rate and other affecting factors in the percolation extraction process are preferably selected, its examining indicators are yield rates of total flavones and dry paste of the main efficacy substances in the extractive, and experimental results are shown in Table 4 to Table 7.

TABLE 4

Pilot factor level table

| Level | A Alcohol concentration (%) | B Alcohol dose (times) | C Blank | D percolation rate (BV/H) |
|---|---|---|---|---|
| 1 | 50 | 8 |  | 2 |
| 2 | 60 | 10 |  | 4 |
| 3 | 70 | 12 |  | 6 |

TABLE 5

Orthogonal Experimental Design and Result Analysis

| Test no. | A | B | C | D | Amount of total flavones in Jinzuan (mg) | Dry paste yield rate (%) |
|---|---|---|---|---|---|---|
| 1 | 1 | 1 | 1 | 1 | 1178.441 | 19.69 |
| 2 | 1 | 2 | 2 | 2 | 1204.917 | 19.86 |
| 3 | 1 | 3 | 3 | 3 | 1286.992 | 20.35 |
| 4 | 2 | 1 | 2 | 3 | 1133.432 | 18.14 |
| 5 | 2 | 2 | 3 | 1 | 1239.336 | 18.98 |
| 6 | 2 | 3 | 1 | 2 | 1268.459 | 19.16 |
| 7 | 3 | 1 | 3 | 2 | 1085.775 | 17.28 |
| 8 | 3 | 2 | 1 | 3 | 1173.146 | 17.27 |
| 9 | 3 | 3 | 2 | 1 | 1318.763 | 18.71 |
| aK1 | 1223.45 | 1132.55 | 1206.68 | 1245.51 | | |
| aK2 | 1213.74 | 1205.8 | 1219.04 | 1186.38 | | |
| aK3 | 1192.56 | 1291.41 | 1204.03 | 1197.86 | | |
| aR | 30.889 | 158.856 | 15.003 | 59.129 | | |
| bK1 | 19.967 | 18.37 | 18.707 | 19.127 | | |
| bK2 | 18.76 | 18.703 | 18.903 | 18.767 | | |
| bK3 | 17.753 | 19.407 | 18.87 | 18.587 | | |
| bR | 2.214 | 1.037 | 0.196 | 0.54 | | |

TABLE 6

Variance Analysis of Total Flavones

| Factor | Sum of squares of deviations | Degree of freedom | Mean square | F value | P |
|---|---|---|---|---|---|
| A | 1496.98 | 2 |  | 3.891 |  |
| B | 37928.844 | 2 |  | 98.579 | <0.05 |
| D | 5899.105 | 2 |  | 15.332 |  |
| Blank (error) | 384.75 | 2 |  |  |  |

$F_{0.05(2,2)} = 19.00$

TABLE 7

Variance Analysis of Dry Paste Yield Rate

| Rate | Sum of squares of deviations | Degree of freedom | Mean square | F value | P |
|---|---|---|---|---|---|
| A | 7.368 | 2 | | 111.636 | <0.05 |
| B | 1.680 | 2 | | 25.455 | <0.05 |
| D | 0.454 | 2 | | 6.879 | |
| Blank (error) | 0.07 | 2 | | | |

$F_{0.05(2,2)} = 19.00$
$F_{0.01(2,2)} = 99.00$

Experimental results show that the biggest affecting factor is the dose of alcohol, followed by alcohol concentration, percolation rate is of no significant impact, and combining visual analysis and variance analysis, the optimum process condition $A_1B_3D_1$, i.e. 12 times the amount of 50% alcohol is added and percolation is conducted at a rate of 2 BV/H, is preferred.

(2) Verification test: In accordance with the optimum condition preferably selected with the orthogonal design test, repeatable tests are conducted in 3 times, and the experimental results are shown in Table 8.

TABLE 8

Verification Test Results of Percolation Extraction

| Test no. | Medicine dosage (g) | Amount of total flavones in Jinxuan (mg) | Dry paste yield rate (%) |
|---|---|---|---|
| 1 | 50 | 1381.77 | 20.80 |
| 2 | 50 | 1331.77 | 20.45 |
| 3 | 50 | 1334.896 | 20.60 |

Verification results show that the extraction process preferably selected is stable and plausible.

Example 2

Macroporous Resin Purification Process Test in the Preparation Method of Alcohol Extractive of the Three Flavors of Botanicals in the Jinxuan Hemorrhoid Washing Powder Prescription The following purification test is conducted to the percolate extracting solution of the three flavors of botanicals of Jinxuan Hemorrhoid Washing Powder obtained through the aforementioned extracting conditions:

(1) D101 Macroporous Resin Purification Process Test

① Preferable Selection of Absorption Conditions

Orthogonal test method is employed, using sampling flow velocity, drug solution concentration (by the original medicinal material amount contained in the sample, namely drug solution concentration=medicinal powder weight/filtrate volume×100%) and the diameter-height ratio as investigated factors, and the test is arranged applying $L_9$ ($3^4$) orthogonal table with factor and level arrangements shown in Table 6. Contents of total flavones, total saponins, and total organic acid in the following 9 groups are measured respectively, its ratio of adsorption is measured, and comprehensive evaluation is conducted. Analysis results are shown in Tables 9~13.

TABLE 9

Factor and Level Table

| Level | A Sampling concentration (g · mL$^{-1}$) | B Absorption flow velocity (BV/H) | C Blank | D Diameter-height ratio |
|---|---|---|---|---|
| 1 | 0.1 | 2 | | 1:3 |
| 2 | 0.3 | 4 | | 1:8 |
| 3 | 0.5 | 6 | | 1:12 |

TABLE 10

Percolate Extracting Solution of Jinxuan Hemorrhoid Washing Powder
Absorption Orthogonal Test Design and Result Analysis Table

| Test no. | A | B | C | D | Ratio absorptiom amount of total flavones (mg · g$^{-1}$) | Ratio absorptiom amount of total saponins (mg · g$^{-1}$) | Ratio absorptiom amount of total organic acid (mg · g$^{-1}$) |
|---|---|---|---|---|---|---|---|
| 1 | 1 | 1 | 1 | 1 | 27.9802 | 3.4808 | 6.4768 |
| 2 | 1 | 2 | 2 | 2 | 25.6412 | 4.4925 | 6.677 |
| 3 | 1 | 3 | 3 | 3 | 24.7292 | 5.507 | 5.8394 |
| 4 | 2 | 1 | 2 | 3 | 30.0425 | 6.083 | 13.1014 |
| 5 | 2 | 2 | 3 | 1 | 31.1506 | 8.9516 | 12.1938 |
| 6 | 2 | 3 | 1 | 2 | 29.9781 | 9.77 | 22.828 |
| 7 | 3 | 1 | 3 | 2 | 33.6501 | 14.9129 | 20.8562 |
| 8 | 3 | 2 | 1 | 3 | 31.1507 | 13.8162 | 8.033 |
| 9 | 3 | 3 | 2 | 1 | 30.2089 | 13.1321 | 8.7032 |
| aK1 | 26.117 | 30.558 | 29.703 | 29.780 | | | |
| aK2 | 30.390 | 29.314 | 28.631 | 29.756 | | | |
| aK3 | 31.670 | 28.305 | 29.843 | 28.641 | | | |
| aR | 5.553 | 2.253 | 1.212 | 1.139 | | | |
| bK1 | 4.493 | 8.159 | 9.022 | 8.521 | | | |
| bK2 | 8.268 | 9.087 | 7.903 | 9.725 | | | |
| bK3 | 13.954 | 9.470 | 9.790 | 8.469 | | | |
| bR | 9.461 | 1.311 | 1.887 | 1.256 | | | |
| cK1 | 6.331 | 13.478 | 12.446 | 9.125 | | | |
| cK2 | 16.041 | 8.968 | 9.494 | 16.787 | | | |
| cK3 | 12.531 | 12.457 | 12.963 | 8.991 | | | |
| R | 9.710 | 4.510 | 3.469 | 7.796 | | | |

TABLE 11

Variance Analysis of Ratio Absorption Amount of Total Flavones of Jinxuan Hemorrhoid Washing Powder

| Factor | Sum of squares of deviations | Degree of freedom | F value | Significance |
|---|---|---|---|---|
| Sampling concentration | 50.736 | 2 | 19.225 | <0.05 |
| Absorption flow velocity | 7.636 | 2 | 2.894 | |
| Diameter-height ratio | 2.543 | 2 | 0.964 | |
| Error | 2.64 | 2 | | |

$F_{0.05(2,2)} = 19$,
$F_{0.01(2,2)} = 99.00$

TABLE 12

Variance Analysis of Ratio Absorption Amount of Total Saponins of Jinxuan Hemorrhoid Washing Powder

| Factor | Sum of squares of deviations | Degree of freedom | F value | Significance |
|---|---|---|---|---|
| Sampling concentration | 136.071 | 2 | 25.161 | <0.05 |
| Absorption flow velocity | 2.726 | 2 | 0.504 | |
| Diameter-height ratio | 3.030 | 2 | 0.560 | |
| Error | 5.41 | 2 | | |

$F_{0.05(2,2)} = 19$,
$F_{0.01(2,2)} = 99.00$

TABLE 13

Variance Analysis of Ratio Absorption Amount of Total Organic Acids of Jinxuan Hemorrhoid Washing Powder

| Factor | Sum of squares of deviations | Degree of freedom | F value | Significance |
|---|---|---|---|---|
| Sampling concentration | 145.043 | 2 | 6.901 | |
| Absorption flow velocity | 33.558 | 2 | 1.597 | |
| Diameter-height ratio | 119.506 | 2 | 5.686 | |
| Error | 21.02 | 2 | | |

$F_{0.05(2,2)} = 19$,
$F_{0.01(2,2)} = 99.00$

The variance analysis results show that sampling concentration (A) has significant effect in the absorption process of alcohol extractive—total flavones, total saponins, and total organic acids, of the three flavors of botanicals in the prescription of Jinxuan Hemorrhoid Washing Powder. Visual analysis shows that absorption flow velocity and diameter-height ratio are of no significant impact, and the optimum process parameter obtained by comprehensive analysis is: $A_3B_1D_2$, i.e. sampling concentration is 0.5 g/ml, absorption flow velocity is 2 BV/H, and diameter-height ratio is 1:8.

Figure 2:
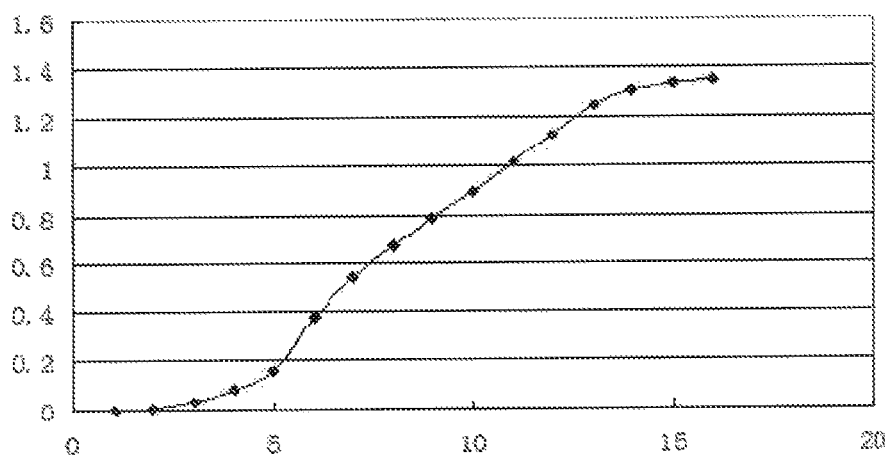
FIG. 2 is the leakage curve of the absorbed total flavones when the sample solution, which is prepared by 70% alcohol percolation extraction of the medicinal powder obtained from supercritical extraction of the three flavors of the botanicals in a Jinxuan Hemorrhoid Washing Powder prescription, goes through the D101 macroporous resin column.

② Sampling Amount Examination 0.5 g/ml Jinxuan percolate is added to the upper end of the 20 g handled D101 resin column, and absorbed according to the optimum adsorption conditions, and the effluent is collected with every 10 mL as one flow fraction. As verified by the pre-test, flavones is first leaked, so the total flavones amount is measured and the leakage curve is drawn with fraction number as the horizontal axis and the absorbance of total flavones as the vertical axis. The result is shown in FIG. 2. It can be seen in the figure that when the sampling amount is 30 mL (about 1.5 times the amount of resin), the total flavones starts to leak, and when the sampling amount is 160 mL (about 8 times the amount of resin), the adsorption reaches its saturation.

③ Washing Condition Examination

Sampling adsorption is conducted according to the aforementioned optimum adsorption conditions with a sampling amount of 30 mL, then washed with water, every 10 mL out-let solution is collected as one flow fraction and identified with molish reaction and Liebermann reaction examination knowledge, the dry paste weight is simultaneously determined, after 60 mL washing, molish reaction and Liebermann reaction are negative, the dry paste weight stops changing, and results show that after washing with 60 mL water (about three times the resin column volume) the sugars in the resin column can be substantially removed.

④ Alcohol Elution Concentration Examination

Another five parts of 20 g resin are loaded, absorbed and removed impurity according to the aforementioned absorption conditions and washing conditions, then eluted with 90 mL 30%, 50%, 70%, and 90% alcohol respectively at the same flow velocity, contents and the desorption rate of the total flavones, total saponins, and total organic acids are calculated, and the results are shown in Tables 14, 15 and 16.

TABLE 14

Alcohol Elution Concentration Examination Results of Total Flavones of Jinxuan Hemorrhoid Washing Powder

| Alcohol concentration (%) | Desorption rate of total flavones (mg) | Desorption rate (%) | Dry paste weight (mg) | Total flavones purity (%) |
|---|---|---|---|---|
| 30 | 130.02 | 40.79 | 625.1 | 20.8 |
| 50 | 285 | 78.5 | 785.2 | 36.3 |
| 70 | 288.1 | 80.3 | 807 | 35.7 |
| 90 | 299.6 | 85 | 886.4 | 33.8 |

TABLE 15

Alcohol Elution Concentration Examination Results of Total Saponins of Jinxuan Hemorrhoid Washing Powder

| Alcohol concentration (%) | Desorption rate of total saponins (mg) | Desorption rate (%) | Dry paste weight (mg) | Total saponins purity (%) |
|---|---|---|---|---|
| 30 | 40.3 | 33.81 | 625.1 | 6.45 |
| 50 | 85.6 | 71.5 | 785.2 | 10.9 |
| 70 | 95.5 | 80.12 | 807 | 11.83 |
| 90 | 98.3 | 82.47 | 886.4 | 11.08 |

TABLE 16

Alcohol Elution Concentration Examination Results of Total Organic Acids of Jinxuan Hemorrhoid Washing Powder

| Alcohol concentration (%) | Desorption rate of total organic acids (mg) | Desorption rate (%) | Dry paste weight (mg) | Total saponins acids purity (%) |
|---|---|---|---|---|
| 30 | 40.63 | 60.3 | 625.1 | 6.5 |
| 50 | 70.67 | 73.5 | 785.2 | 9 |

TABLE 16-continued

Alcohol Elution Concentration Examination Results of Total Organic Acids of Jinxuan Hemorrhoid Washing Powder

| Alcohol concentration (%) | Desorption rate of total organic acids (mg) | Desorption rate (%) | Dry paste weight (mg) | Total saponins acids purity (%) |
|---|---|---|---|---|
| 70 | 126 | 78.1 | 807 | 15.71 |
| 90 | 101.9 | 80 | 886.4 | 11.5 |

The above test results show that both the desorption rate and content of the total flavones, total saponins, and total organic acids are relatively high when the concentration of the alcohol is above 50%, wherein the desorption rate of total flavones, total saponins, and total organic acids in 90% alcohol elution is the highest, while the purity of total saponins, and total organic acids in 70% alcohol elution is the highest. After comprehensive analysis, taking into account that the desorption rate of 70% alcohol differentiates not that much from that of 90% alcohol, and the production costs are relatively low, therefore 70% alcohol is selected as the eluent of the present test.

⑤ Elution Rate Examination

Dynamic adsorption is conducted according to the above conditions, with 70% alcohol as eluent, eluted at a velocity of 1 BV·H$^{-1}$, 2 BV·H$^{-1}$, 4 BV·H$^{-1}$, and 6 BV·H$^{-1}$ respectively, the amount of total flavones, total saponins, total organic acids and dry paste weight are measured and the desorption rate and purity are calculated, and the results are shown in Tables 17, 18, and 19.

TABLE 17

Alcohol Elution Rate Examination of Total Flavones of Jinxuan Hemorrhoid Washing Powder

| Elution flow velocity | Elution amount of total flavones (mg) | Desorption rate (%) | Total flavones purity in the dry paste (%) | Dry paste weight (mg) |
|---|---|---|---|---|
| 1BV/H | 311.2 | 81 | 37 | 841.1 |
| 2BV/H | 296.17 | 80.49 | 36.7 | 807 |
| 4BV/H | 240.76 | 79.1 | 30.69 | 784.5 |
| 6BV/H | 202.2 | 59 | 28.8 | 702.1 |

TABLE 18

Alcohol Elution Rate Examination of Total Saponins of Jinxuan Hemorrhoid Washing Powder

| Elution flow velocity | Elution amount of total sanopins (mg) | Desorption rate (%) | Total saponins purity in the dry paste (%) | Dry paste weight (mg) |
|---|---|---|---|---|
| 1BV/H | 96.4 | 82 | 11.46 | 841.1 |
| 2BV/H | 95.03 | 79.8 | 11.78 | 807 |
| 4BV/H | 93.7 | 75.3 | 11.94 | 784.5 |
| 6BV/H | 80.35 | 63.7 | 11.4 | 702.1 |

TABLE 19

Alcohol Elution Rate Examination of Total Organic Acids of Jinxuan Hemorrhoid Washing Powder

| Elution flow velocity | Elution amount of total organic acids (mg) | Desorption rate (%) | Total organic acids purity in the dry paste (%) | Dry paste weight (mg) |
|---|---|---|---|---|
| 1BV/H | 130.25 | 77.2 | 15.49 | 841.1 |
| 2BV/H | 121.41 | 75 | 15.04 | 807 |
| 4BV/H | 110.05 | 73.8 | 14.03 | 784.5 |
| 6BV/H | 80.49 | 69 | 11.46 | 702.1 |

Results show that at the flow velocity of 1 BV/H, the elution effect is relatively good, the purity and desorption rate are both relatively high. After comprehensive analysis, an elution flow velocity of 1 BV/H is selected.

⑥ Alcohol Elution Amount Examination

Figure 3:
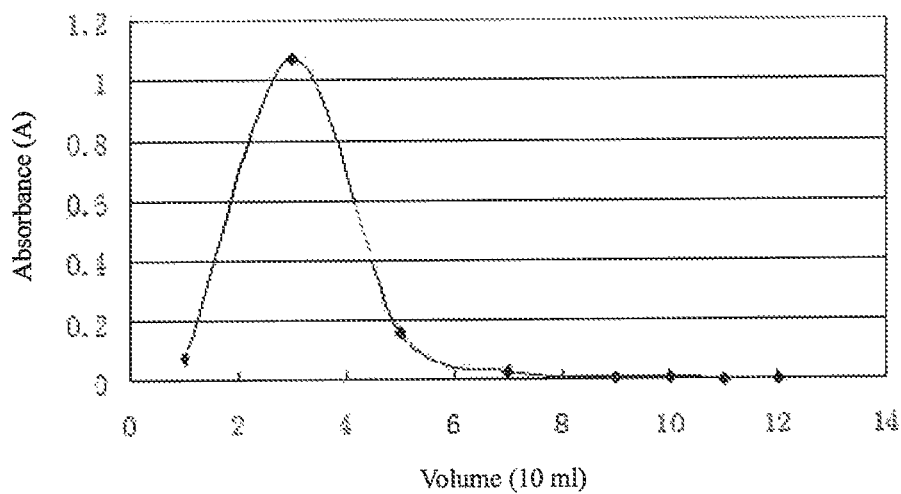
FIG. 3 is the eluting curve of the total flavones in an eluting resin column using 70% alcohol as its eluent.
Figure 4:
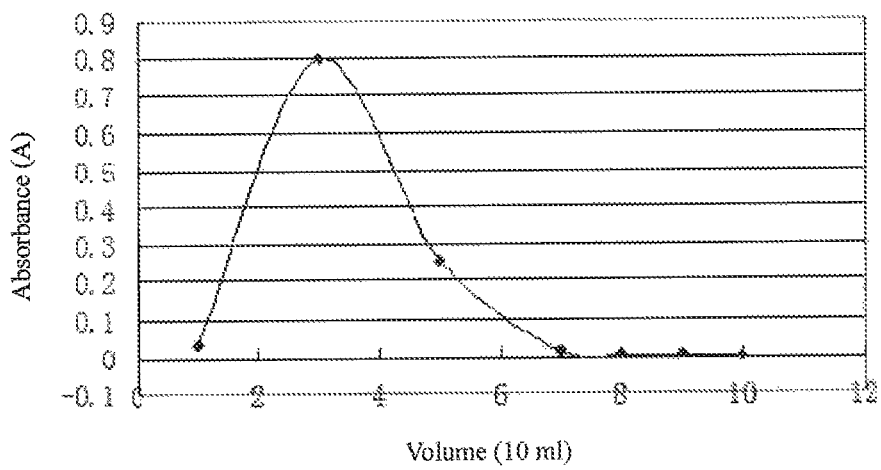
FIG. 4 is the eluting curve of the total saponins in an eluting resin column using 70% alcohol as its eluent.
Figure 5:
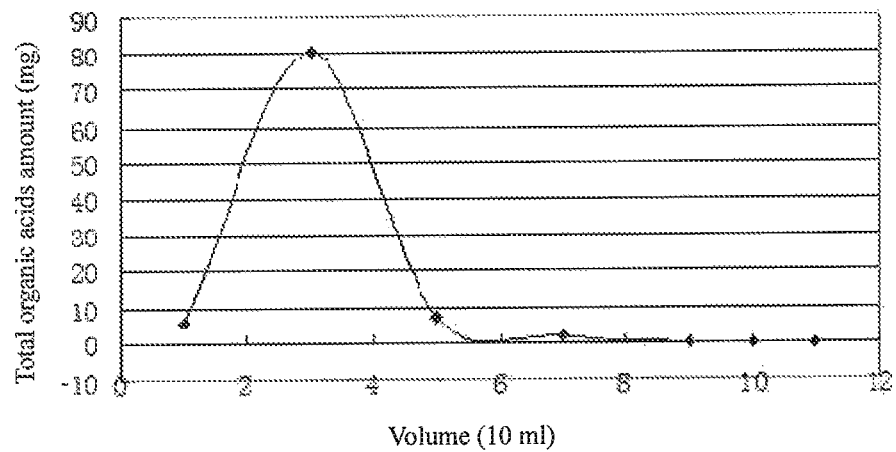
FIG. 5 is the eluting curve of the total organic acids in an eluting resin column using 70% alcohol as its eluent.

Dynamic adsorption is conducted according to the above conditions, with 70% alcohol as eluent, eluted at a velocity of 1 BV·H$^{-1}$, the amount of total flavones, the out-let solution is collected at a certain volume and total saponins, total organic acids are measured, and elution curve is drawn. The results are shown in FIG. 3, FIG. 4 and FIG. 5.

Results show that flavonoids compositions absorbed by 20 g resin can be completely eluted with 100 mL (about 5 times the amount of resin) 70% alcohol; saponins compositions absorbed by 20 g resin can be completely eluted with 90 mL (about 4.5 times the amount of resin) 70% alcohol; organic acids compositions absorbed by 20 g resin can be completely eluted with 100 mL (about 5 times the amount of resin) 70% alcohol. So using 100 mL (5 times the amount of resin) 70% alcohol at a flow velocity of 1 Bv/h can make flavonoids, saponins and organic acids compositions absorbed by 20 g resin completely eluted.

The final preferred purification process condition parameters are: Resin Model: D101; sampling volume: the ratio between the medicinal powder amount and the resin amount is 0.75:1; sampling concentration: relatively more precipitate is produced and the loss is relatively large when sampling at a concentration of 0.5 g/ml, so the sampling concentration of 0.3 g/ml is finally selected. Adsorption rate: 2 BV/H; diameter-height ratio: 1:8; water washing amount: 3 BV; alcohol wash concentration: 70%; alcohol washing speed: 1 BV/H; alcohol washing amount: 5 BV.

Example 3

Pilot Plant Enlargement Test 7.5 Kg medicinal powder obtained from supercritical $CO_2$ extraction of the three flavors of Jinxuan Hemorrhoid Washing Powder botanicals (which is mixed at a ratio of 3:4:3, ground, and passed through a 40 mesh) is added with a 50% alcohol aqueous solution with a weight of 3 times that of the medicinal powder and soaked for 24 hours, and then a 50% alcohol aqueous solution is added to make the weight of the 50% alcohol aqueous solution equal to 12 times the weight of the medicinal powder, the percolation extraction is underwent with a flow velocity of the weight of 2 times that of the medicinal powder per hour, and the percolate is collected; the percolate is concentrated to a certain volume to make the weight of the drug solution equal to 3.3 times that of said medicinal powder (25 L), and suction filtrated to obtain a sampling drug solution.

10 Kg medical grade D101 macroporous resin is soaked with an appropriate amount of alcohol, wet packed and handled for future use.

3.2.1 Adjustment of Test Parameters

During pilot plant enlargement, both the sampling amount and flow velocity are enlarged by 1000 times, thus test parameters need to be timely adjusted according to the test results. Different absorption and water washing rates are employed to examine its purification effect, and the results are shown in Table 20.

TABLE 20

Flow Velocity Examination Table

| Velocity (BV/H) | Coagulant dose (Kg) | Extractive (mg) | Extract collection rate (%) | Transfer rate of total flavones (%) | Total flavones purity (%) | Transfer rate of total saponins (%) | Total saponins purity (%) | Transfer rate of total organic acids (%) | Total acids purity (%) |
|---|---|---|---|---|---|---|---|---|---|
| 4 | 7.5 | 262.5 | 3.5 | 59.2 | 30.5 | 60.6 | 12.2 | 57.7 | 14.8 |
| 2 | 7.5 | 315 | 4.2 | 67.5 | 33.1 | 71.6 | 15.7 | 69.1 | 18.6 |
| 1 | 7.5 | 375 | 5 | 78 | 34.8 | 79.3 | 13.1 | 73.4 | 19.7 |
| 0.5 | 7.5 | 412.5 | 5.5 | 80 | 36.7 | 81.4 | 17.4 | 78 | 21.3 |

Results show that the content and transfer rate of total flavones, total saponins, and total organic acids are relatively high when the flow velocity is 1 time the column volume per hour. Therefore, the sampling and water washing flow velocity is determined to be 1 $BV \cdot H^{-1}$.

3.2.2 Experimental Method and Results

An appropriate amount of the three flavors of botanicals—honeysuckle, schizonepeta, and purslane in the prescription of Jinxuan Hemorrhoid Washing Powder are mixed at a weight ratio of 3:4:3, ground, passed through a 40 mesh, and supercritically $CO_2$ extracted to obtain the medicinal powder. 7.5 Kg medicinal powder is added with 50% alcohol and soaked for 24 hours, 50% alcohol with a weight of 12 times the weight of the medicinal powder is added, the percolation extraction is underwent at a flow velocity of 2 BV/H, the percolate is collected, alcohol is recovered by reduced pressure to a certain volume, and suction filtrated to obtain the sampling drug solution.

10 Kg medical grade D101 macroporous resin is soaked with an appropriate amount of alcohol, wet packed and washed with a large amount of alcohol, out-let solution is constantly detected until when mixed with water white precipitation is not exhibited. Then alcohol is washed with a large amount of distilled water for future use.

The absorption is conducted at a sampling flow velocity of 1 Bv/h with resin bed diameter-height ratio of 1:8, washed with 3 BV distilled water after the completion of absorption at a flow velocity of 1 Bv/h till the molish reaction exhibiting negative, and then underwent elution with 70% alcohol with a volume of 5 times that of the resin column at a flow velocity of 1 Bv/h to obtain the eluent; the eluent is concentrated to a relative density of 1.03, and spray dried (at inlet temperature of 170° C., outlet temperature of 90° C., and atomizing disk rotation speed of 20,000 RIM). The dried extraction is collected, sealed, weighed, and preserved in shade place.

Ultraviolet—visible spectrophotometry is employed to measure the amount of total flavones in the extractive, Transfer rate (transfer rate=the amount of total flavones in the extractive/he amount of total flavones in the raw medical material×100%) and cream collection rate (cream collection rate=total extractive weight/total raw medical material weight×100%) are calculated. The results are shown in Table 21.

TABLE 21

Pilot Plant Test Results

| Test batch | Coagulant dose (Kg) | Extractive (mg) | Extract collection rate (%) | Transfer rate of total flavones (%) | Total flavones purity (%) | Transfer rate of total saponins (%) | Total saponins purity (%) | Transfer rate of total organic acids (%) | Total acids purity (%) |
|---|---|---|---|---|---|---|---|---|---|
| 1 | 7.5 | 330 | 4.4 | 75.2 | 34.8 | 80.2 | 15.2 | 72.7 | 19.8 |
| 2 | 7.5 | 352.5 | 4.7 | 78.5 | 35.1 | 79.6 | 15.5 | 76.1 | 20.6 |
| 3 | 7.5 | 397.5 | 5.3 | 81.0 | 35.8 | 82.3 | 15.7 | 78.4 | 20.7 |
| Average | 7.5 | 360 | 4.8 | 78.2 | 35.2 | 80.7 | 15.5 | 75.7 | 20.4 |

Results show that the total content of flavones, saponins, and organic acids in the extractives of the three batches can exceed 70%, which shows that the present experimental research has plausible process parameters and can be transited to industrialized production after further pilot plant adjustment of the process conditions.

The invention claimed is:
1. A preparation method, comprising the following steps:
    mixing three ingredients including honeysuckle, schizonepeta, and purslane into a mixed powder at a weight ratio of 3:4:3, respectively;
    grinding and sifting the powder through a 30-50 mesh, performing a supercritical extraction of the powder, adding the powder after supercritical extraction to a first alcohol aqueous solution with a weight of 2-4 times that of said powder and a volume ratio of 30-90% and soaking the solution and the powder for 20-30 hours, and then an second alcohol aqueous solution with a volume ratio of 30-90% is added to make the weight of the first alcohol aqueous solution with a volume ratio of 30-90% equal to 6-14 times the weight of said powder;

performing percolation extraction is with a flow velocity of the weight of 1-5 times that of said powder per hour, and collecting a resulting alcohol percolate;

concentrating the alcohol percolate to a weight of 1-5 times that of said powder, leaving the alcohol percolate to stand for 2-10 hours, and suction filtering the alcohol percolate to obtain a filtrate;

purifying the filtrate by macroporously absorbing the filtrate into a resin column at a flow velocity of a volume of 0.5-4 times that of the column per hour, by washing the resin column with water with a volume of 2-4 times that of the column, wherein the filtrate undergoes elution with an alcohol aqueous solution with a volume ratio of 40-95% and a flow velocity of a volume of 0.5-4 times that of the column per hour to obtain an alcohol eluent; and recovering alcohol from the alcohol eluent, concentrating any remaining liquid, and drying a resulting concentrated liquid to obtain an extractive of the ingredients.

2. The preparation method according to claim 1, wherein the powder obtained from mixing the three ingredients is added with an alcohol aqueous solution with a weight of 3 times that of said and a volume ratio of 50% and soaked for 24 hours, and then an alcohol aqueous solution with a volume ratio of 50% is added to make the weight of the alcohol aqueous solution with a volume ratio of 50% equal to 12 times the weight of said powder, percolation extraction is performed with flow velocity of the weight of 2 times that of said powder per hour, and then the resulting alcohol percolate is collected.

3. The preparation method according to claim 1, wherein the alcohol percolate obtained is concentrated to a weight of 3.3 times that of said powder.

4. The preparation method according to claim 1, wherein the filtrate macroporously absorbs into a resin column at a flow velocity of a volume of 1 time that of the column per hour, is then purified by washing with water with a volume of 3 times that of the column, and undergoes elution with an alcohol aqueous solution with a volume ratio of 70% and a flow velocity of a volume of 1 time that of the column per hour.

5. The preparation method according to claim 1, wherein drying the concentrated liquid is spray drying with conditions, including: inlet temperature of 170° C., outlet temperature of 90° C., and atomizing disk rotation speed of 20,000 R/M.

6. The preparation method according to claim 1, wherein said resin column is a medical type D101 type macroporous resin column.

7. The preparation method according to claim 1, wherein a diameter-height ratio of said resin column is 1:3-1:8.

8. The preparation method according to claim 1, wherein before mixing, the three ingredients are placed in a supercritical $CO_2$ extraction device with extraction temperature of 45° C., extraction pressure of 25 MPa and extraction time of 90 min.

* * * * *